(12) United States Patent
Brovelli et al.

(10) Patent No.: US 6,306,443 B1
(45) Date of Patent: Oct. 23, 2001

(54) METHOD OF INCREASING CONCENTRATIONS OF CAFFEIC ACID DERIVATIVES AND ALKYLAMIDES AND COMPOSITIONS CONTAINING THE SAME

(75) Inventors: Ernesto A. Brovelli, Corona; Rodney Johnson, Temecula, both of CA (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/598,417

(22) Filed: Jun. 20, 2000

(51) Int. Cl.[7] .................................................. A01N 65/00
(52) U.S. Cl. ................................................................ 424/725
(58) Field of Search .............................. 424/195.1, 725; 435/420, 430, 431

(56) References Cited

U.S. PATENT DOCUMENTS

| | | |
|---|---|---|
| 4,857,512 | 8/1989 | Wagner et al. . |
| 5,248,503 | 9/1993 | Emanuel-King . |
| 5,455,033 | 10/1995 | Silverman et al. . |
| 5,656,310 | 8/1997 | Santillo, Jr. . |
| 5,876,728 | 3/1999 | Kass et al. . |
| 5,939,071 | 8/1999 | Joseph . |
| 6,019,977 | 2/2000 | Joseph . |
| 6,027,716 | 2/2000 | Levin et al. . |
| 6,027,757 | 2/2000 | Menon . |

FOREIGN PATENT DOCUMENTS

| | | |
|---|---|---|
| 679162 B | 6/1997 | (AU) . |
| 702894 B | 3/1999 | (AU) . |
| 3217214 A | 11/1983 | (DE) . |
| 4438589 | 3/1995 | (DE) . |
| 0 753 306 B1 | 1/1997 | (EP) . |
| 2676648 A | 11/1992 | (FR) . |
| 1229999 | 4/1989 | (IT) . |
| 7017846 A | 1/1995 | (JP) . |
| 11116495 | 4/1999 | (JP) . |
| 11302189 A | 11/1999 | (JP) . |
| 1003751 C | 2/1998 | (NL) . |
| 110907 B | 5/1996 | (RO) . |
| WO98/11778 | 3/1998 | (WO) . |
| WO99/21007 | 4/1999 | (WO) . |
| WO99/21425 | 5/1999 | (WO) . |

OTHER PUBLICATIONS

Wills et al. Alkylamide and Cichoric Acid Levels in *Echinacea purpurea* Grown in Austrailia; Food Chemistry 67, 385–388, Apr. 1999.*

Wills et al. Effect of Handling and Food Storage on Alkylamides and Cichoric Acid in *Echinacea purpurea*; Sci. Food Agric. 80: 1402–1406, Jul. 2000.*

R.B.H. Wills, D.L. Stuart, Alkylamide and Cichoric Acid Levels in *Echinacea Purpurea* Grown in Australia, Food Chemistry 67, 385–388 (1999).

Brigitte H. Schulthess, Eva Giger, andThomas W. Baumann, Echinacea: Anatomy, Phytochemical Pattern, and Germination of the Achene, Planta Med. 57 (1991).

R. Bauer and H. Wagner, Echinacea Species as Potential Immunostimulatory Drugs, Econ. Medic. Plant Res., 5, 253–321, Wagner, H. and Farnsworth, N.R. (Editors), Academic Press Ltd., New York, NY (1991).

* cited by examiner

*Primary Examiner*—Jon P. Weber
*Assistant Examiner*—Patricia A. Patten
(74) *Attorney, Agent, or Firm*—Amy I. Ahn (57) ABSTRACT

A method of increasing the concentration of caffeic acid derivatives, such as cichoric acid, and the concentration of alkylamides, such as tetraene alkylamides, in Echinacea plant postharvest; and a composition, having increased amounts of these phytochemicals per gram of plant material. The method includes the following steps: (1) harvesting a plant having caffeic acid derivatives and alkylamides; (2) separating the plant into fragments; and (3) storing the separated fragments in refrigerated conditions at a controlled relative humidity which prevents wilting and microbial decay. The raw plant material obtained from this process can be used alone or in combination with other nutrients in a medicine or dietary supplement.

13 Claims, 5 Drawing Sheets

METHOD OF INCREASING CONCENTRATIONS OF CAFFEIC ACID DERIVATIVES AND ALKYLAMIDES AND COMPOSITIONS CONTAINING THE SAME

FIELD OF THE INVENTION

The present invention relates to a method of increasing the concentrations of caffeic acid derivatives and alkylamides and compositions containing the same. In particular, the present invention relates to a method for increasing the concentrations of cichoric acid and dodeca-2E, 4E, 8Z, 10E/Z-tetraenoic acid isobutylamide ("tetraene alkylamides"), which are key active phytochemicals in Echinacea, and raw materials containing the same.

BACKGROUND OF THE INVENTION

In recent years, Echinacea has become one of the most popular commercial medicinal herbs in the world (Wills and Stuart, *Alkylamide and Cichoric Acid Levels in Echinacea purpurea Grown in Australia*, Food Chemistry, 67, 385–388 (1999)). Echinacea has received international attention because of its immunostimulatory and other beneficial effects. Although several phytochemicals in Echinacea work together in providing these beneficial effects, caffeic acid derivatives, most notably cichoric acid, and lipophilic alkylamides are indicated as making considerable contributions to Echinaces's immunostimulatory activity (Bauer, R. and Wagner, H., *Echinacea Species as Potential Immunostimulatory Drugs*, Econ. Medic. Plant Res., 5, 253–321, Wagner, H. and Farnsworth, N. R. (Editors), Academic Press Ltd., New York, N.Y. (1991)).

Echinacea is the genus name for nine herbaceous perennial species native to North America. Echinacea, however, usually refers to *Echinacea angustifolia*, *Echinacea purpurea*, or *Echinacea pallida*. Echinacea was first widely used by several North American Indian tribes against various conditions such as wounds, burns, insect bites, headaches, stomach cramps, coughs, and the measles. The primary use of Echinacea is for increasing resistance to infections in the upper respiratory tract and colds in the upper respiratory tract (Bauer, R. and Wagner, H., *Echinacea Species as Potential Immunostimulatory Drugs*, Econ. Medic. Plant Res., 5, 253–321, Wagner, H. and Farnsworth, N. R. (Editors), Academic Press Ltd., New York, N.Y. (1991)). Echinacea has anti-inflammatory and antibacterial activities useful in treating conditions such as skin inflammations and urinary tract infections. It has been indicated that Echinacea also fights cancer by stimulation of key lymphocye production, which triggers natural killer cells to destroy tumor cells (see Lersch, C. et al., *Nonspecific Immunostimulation with Low Doses of Cyclophosphamide, Thymostimulin, and Echinacea purpurea extracts (Echinacin) in Patients with Far Advanced Colorectal Cancer*, Cancer Invest. 10(5): 343–348 (1992)).

Cichoric acid, which is a caffeic acid derivative, and tetraene alkylamides are two types of phytochemicals present in Echinacea that are thought to be primarily responsible for Echinacea's beneficial activity. Cichoric acid, in particular, has been noted to inhibit HIV-1 integrase and replication in tissue culture (Robinson, W. et. al., *Inhibitor of HIV-1 Replication that Inhibit HIV Integrase*, Proc. Natl. Acad. Sci. USA, 93, 6326–6331 (1996)).

The chemical structure of cichoric acid and tetraene alkylamides are shown below:

Dodeca-2E, 4E, 8Z, 10E-tetraenoic acid isobutylamide 1,2-Dicaffeoyl-tartaric acid (Chlcoric acid)

Dodeca-2E, 4E, 8Z, 10Z-tetraenoic acid isobutylamide

Other non-limiting examples of caffeic acid derivatives are echinacoside, verbascoside, chlorogenic acid, isocholorogenic acids, cynarine, and caftaric acid, as shown below.

[Structure: tartaric acid derivative with R1, R2, R3, R4 substituents and cinnamoyl group with R5, R6]

|  | $R_1$ | $R_2$ | $R_3$ | $R_4$ | $R_5$ | $R_6$ |
|---|---|---|---|---|---|---|
| 2-O-Caffeoyl-tartaric acid (Caftaric acid) | H | H | OH | H | — | — |
| 2,3-O(Di-caffeoyl-tartaric acid (Cichoric acid) | H | R' | OH | H | OH | H |
| 2,3-O-Di-caffeoyl-tartaric acid-methylester | $CH_3$ | R' | OH | H | OH | H |
| 2-O-Feruloyl-tartaric acid | H | H | $OCH_3$ | H | — | — |
| 2-O-Caffeoyl-3-O-coumaroyl-tartaric acid | H | R' | OH | H | H | H |
| 2-O-Caffeoyl-3-O-teruloyl-tartaric acid | H | R' | OH | H | $OCH_3$ | H |
| 2,3-O-Di(5-[α-carboxy-β-(3,4-di-hydroxy-phenyl)-ethyl)-caffeoyl]-tartaric acid | H | R' | OH | R' | OH | R' |
| 2-O-Caffeoyl-3-O-(5-[α-carboxy-β-(3,4-dihydroxy-phenyl)-ethyl)-caffeoyl]-tartaric acid | H | R' | OH | H | OH | R' |

[Structure: glycoside with caffeoyl and phenethyl groups]

|  | R | R' |
|---|---|---|
| Echinacoside | Glucose (1,8-) | Rhamnose (1,3-) |
| 6-O-Caffeoyl-echinacoside | 6-O-Caffeoyl-glucose (1,6-) | Rhamnose (1,3-) |
| Verbascoside | H | Rhamnose (1,3-) |
| Dirhamnosyl-verbascoside | H | H |

[Structure: quinic acid derivative with $R_1O$, $R_2O$, $R_3O$, $R_4O$ substituents on cyclohexane]

|  | $R_1$ | $R_2$ | $R_3$ | $R_4$ |
|---|---|---|---|---|
| 3-O-Caffeoyl-quinic acid (Chlorogenic acid) | H | R | H | H |
| Isochlorogenic acids | H | R | R | H |
|  | H | R | H | R |
|  | H | H | R | R |
| Cynarine | R | H | H | R |

[Structure: R' = cinnamoyl group with $R_5$, $R_6$, OH substituents]

Other non-limiting examples of alkylamides in the roots of *E. purpurea* and *E. angustifolia* are shown below:

-continued

16
Undeca-2Z-en-8, 10-diynoic acid 2-methylbutylamide

17
Dodeca-2E-en-8, 10-diynoic acid 2-methylbutylamide

18
Pentadeca-2E, 9Z-dien-12, 14-diynoic acid isobutylamide
(Bohlmann (1943): Echinacea purpurea)

19
Hexadeca-2E, 9Z-dien-12, 14-diynoic acid isobutylamide

It is believed that the root portions of *E. purpurea* provide the highest concentration of alkylamides. The concentration of caffeic acid derivatives are believed to be similar in root and aerial samples. Nonetheless, the concentrations of caffeic acid derivatives and alkylamides may vary from one species of Echinacea to another and may also vary within the same species. The variation of caffeic acid derivatives and alkylamides concentrations within the same species are believed to be partly due to environmental factors, such as the difference in daylight and seasonal change in rainfall.

In the past, to obtain increased amounts of caffeic acid derivatives and alkylamides, one had to grow and harvest more Echinacea plants. Thus, the number of plants having caffeic acid derivatives and alkylamides determined the amount of these phytochemicals available for use in dietary supplements or in other compositions. As a result, more money, time, and effort were involved in producing a commercial product containing these phytochemicals. Therefore, there remains a need to provide a method of increasing the concentrations of caffeic acid derivatives and alkylamides per gram of plant material or, alternatively, a method of making a raw plant material that has increased concentrations of these phytochemicals per gram of plant material. There also remains a need for a composition having increased concentrations of caffeic acid derivatives, such as cichoric acid, and alkylamides, such as tetraene alkylamides, in dietary supplements because of their immunostimulatory and other beneficial effects. The present invention meets the foregoing needs by providing a simple, cost effective method of increasing the concentrations of caffeic acid derivatives (i.e. cichoric acid) and alkylamides (i.e. tetraene alkylamides) in Echinacea and other plants having these phytochemicals as well as compositions containing the same.

SUMMARY OF THE INVENTION

According to the present invention, the foregoing and other objects and advantages are attained by providing a method that involves harvesting a plant having caffeic acid derivatives and alkylamides; separating the plant into fragments; and storing the separated plant fragments in refrigerated conditions at a controlled relative humidity which prevents wilting and microbial decay. The harvesting, separating, and storing steps are collectively referred to as "handling protocol".

The storage process is a surprising aspect of the present invention because it is generally known by those in the plant industry that phytochemicals with medicinal properties are unstable and will degrade overtime. Thus, storing the presumably unstable plant material to achieve higher concentrations of certain phytochemicals would have been illogical.

In accordance with one aspect of the invention, the plant fragments should be stored at the foregoing temperature and humidity conditions for about 24 hours before the fragments are further processed to obtain the greatest increase in alkylamide levels. In accordance with another aspect of the invention, the plant fragments are stored under the above temperature and humidity conditions for about 96 hours, rather than about 24 hours, to obtain the greatest increase in caffeic acid derivatives. However, storage for about 96 hours can comprise the concentration of alkylamides with generally begins to fall after 24 hours of storage.

Accordingly, it is one object of the invention to obtain increased concentrations of caffeic acid derivatives and alkylamides per plant without having to increase the growth and harvest of plants having these phytochemicals. Because this invention allows for a simple method of obtaining increased concentrations of caffeic acids and alkylamides, money and time spent by manufacturers and growers of Echinacea can be substantially reduced. The economic savings from this invention are further enhanced because, except for requiring a refrigerator, the necessary resources are cheap or naturally available in the environment. This invention will allow consumers to receive raw materials having caffeic acid derivatives and alkylamides more readily and at a cheaper price. These and other objects, advantages, and features of the invention will be more readily understood and appreciated by reference drawings and to the detailed description of the invention.

DETAILED DESCRIPTION OF THE INVENTION

In the preferred embodiment, the process includes the following steps: (1) harvesting an Echinacea plant; (2) chopping the plant into fragments; (3) and storing the fragments in refrigerated, semi aerobic conditions at a controlled relative humidity which prevents wilting and microbial decay. The process of the present invention is suitable for any Echinacea species. Other plants, fruits, and vegetables having caffeic acid derivatives and/or alkylamides such as lettuce and endives are contemplated for the present invention.

Figure 1:
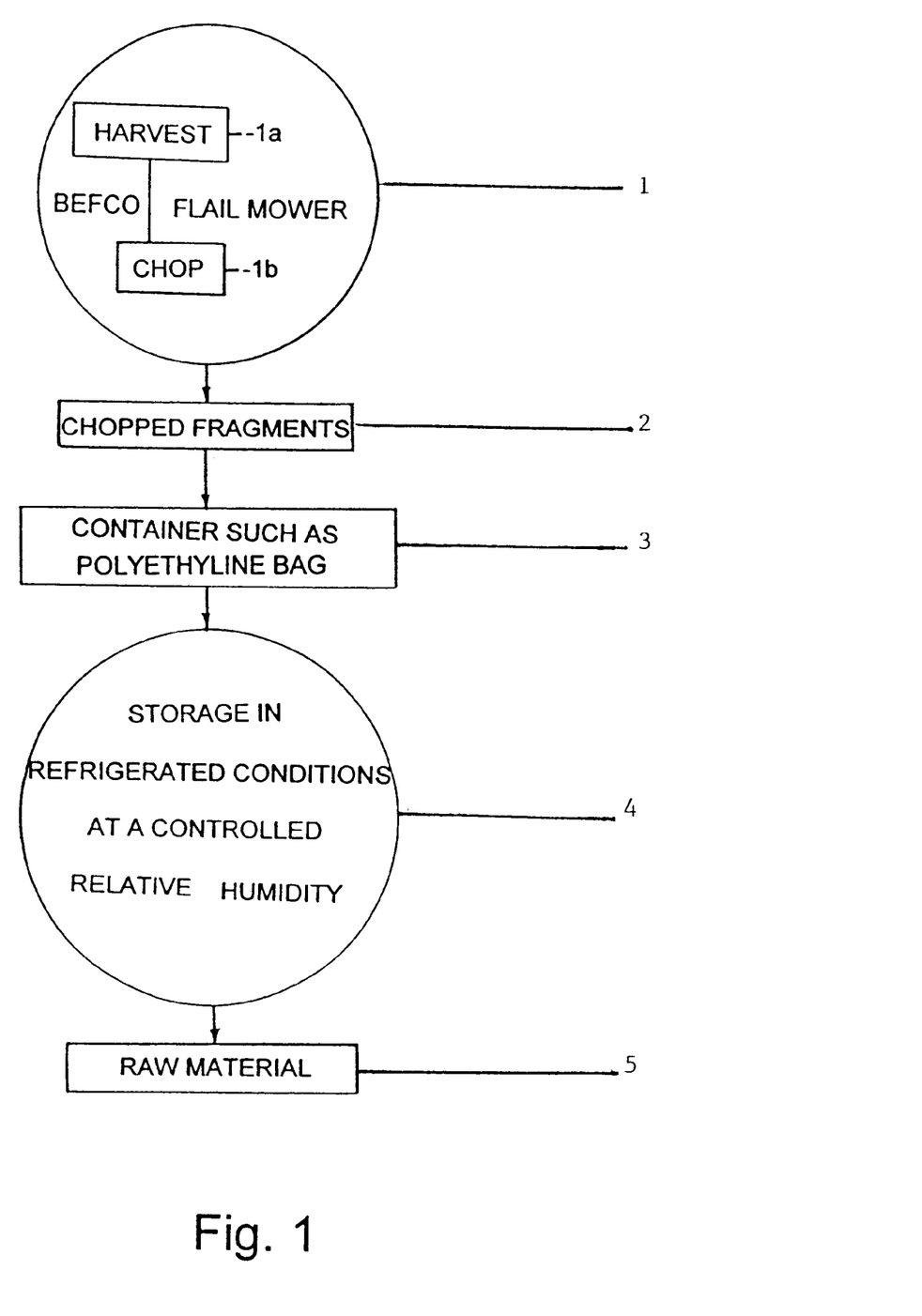
FIG. 1 is a flow chart illustrating the preferred embodiment of the methods in accordance with the present invention.

FIG. 1 illustrates the preferred embodiment of the methods of the present invention. It is preferred that an Echinacea plant is grown and harvested when the crop has bloomed with more than 50% of the flowers being fully developed. It is preferred that the plant is harvested at least 5 inches from the ground. However, it is also contemplated that the entire plant, including the root portions, are harvested. Once harvested, the plant should be separated into fragments, preferably by chopping. One of skill in the art can appreciate that various chop sizes can be utilized while still conforming to the objects of the invention. Although overall levels of caffeic acid derivatives and alkylamides are generally higher in the root portions of the plant, the entire plant or the aerial portions alone can be chopped.

It is preferred that a Befco Flail Mowe 1 simultaneously performs the harvesting 1*a* and chopping 1*b* processes. Thus, the elapsed time between harvesting and chopping is minimized which allows for the freshly chopped plant fragments to be quickly stored to prevent the possibility of decay or loss in caffeic acid derivatives and/or alkylamides. Other suitable machines for harvesting and chopping the plant include an Urschel chopper (Comitrol) having a 0.24 inch (0.61 cm) mill head, and a Good Nature EG400/50 Crop Chopper.

The chopped plant fragments 2 are next placed in a polyethylene bag 3. It is preferable that the polyethylene bag has openings, whereby contents placed within the bag are exposed to air. Other storage containers, such as a paper bag or a burlap bag, can be used in place of the polyethylene bag to achieve a semi-aerobic atmospheric condition within the container. Most preferably, approximately 40 kilograms of fresh plant fragments should be stored in a 40 kilogram polyethylene bag having several 2 to 3 inch slits. The polyethylene bag is then stored 4 in refrigerated conditions at a controlled relative humidity to prevent wilting and microbial decay.

It is preferred that the plant fragments are stored at less than about 10 degrees Celsium with a relative humidity of about 40% to about 85%. More preferably, the plant fragments should be stored at about 0 to about 8 degrees Celsius with a relative humidity level of about 50% to about 85%. Even more preferably, the plant fragments should be stored at about 5 degrees Celcius with a relative humidity level of about 60% to about 85%. Most preferably, the plant fragments should be stored at about 3 degrees Celsius with a relative humidity of about 84%.

The foregoing temperature and humidity conditions should be applied for about 12 hours to about 100 hours. More preferably, the above temperature and humidity conditions should be applied for about 22 to about 96 hours. After about 24 hours, the increase in concentration of alkyamides tends to decline, but the concentration of caffeic acid derivatives continues to increase until about 96 hours. Accordingly, to obtain an increase in both caffeic acid derivatives and alkylamides for plant fragments within the same container, the container should undergo the above temperature and humidity conditions for about 24 hours. However, to obtain the greatest increase in caffeic acid derivatives alone, the above temperature and humidity conditions should be applied for about 96 hours. A portion of the plant fragments that are harvested and separated can be stored for about 24 hours and the remaining portion of the total plant fragments can be stored for about 96 hours to obtain the greatest concentrations of caffeic acid derivatives and aklylamides.

The foregoing steps provide a raw material 5 that has increased concentrations of caffeic acid derivatives and alkylamides as compared to the original postharvest concentrations. This raw material can be sold to manufacturers for use in dietary supplements or other compositions. The raw material can also be further processed to form a liquid or powder. Final processing steps may include blanching and juicing, or dehydration and solvent extraction. These steps can be performed using any particular process. For example U.S. Pat. No. 6,027,757 to Menon demonstrates a method of blanching and drying plants and is incorporated in its entirety by reference. Alternatively, one can perform serial extractions on the raw material to achieve desired purity levels of caffeic acid derivatives and alkylamides prior to the above final processing steps or prior to other uses. The liquid or powder Echinacea can be used in combination with nutrients and/or medicinal compositions to form a dietary supplement in the form of a powder, liquid, tablet, or capsule. The supplement can be effective to help treat various conditions, such as upper respiratory tract infections, inflammatory illnesses, stomach cramps, and coughs.

The following example is presented for the purpose to further illustrating and explaining the present invention and is not to be taken as limiting in any regard.

EXAMPLE

Figure 2:
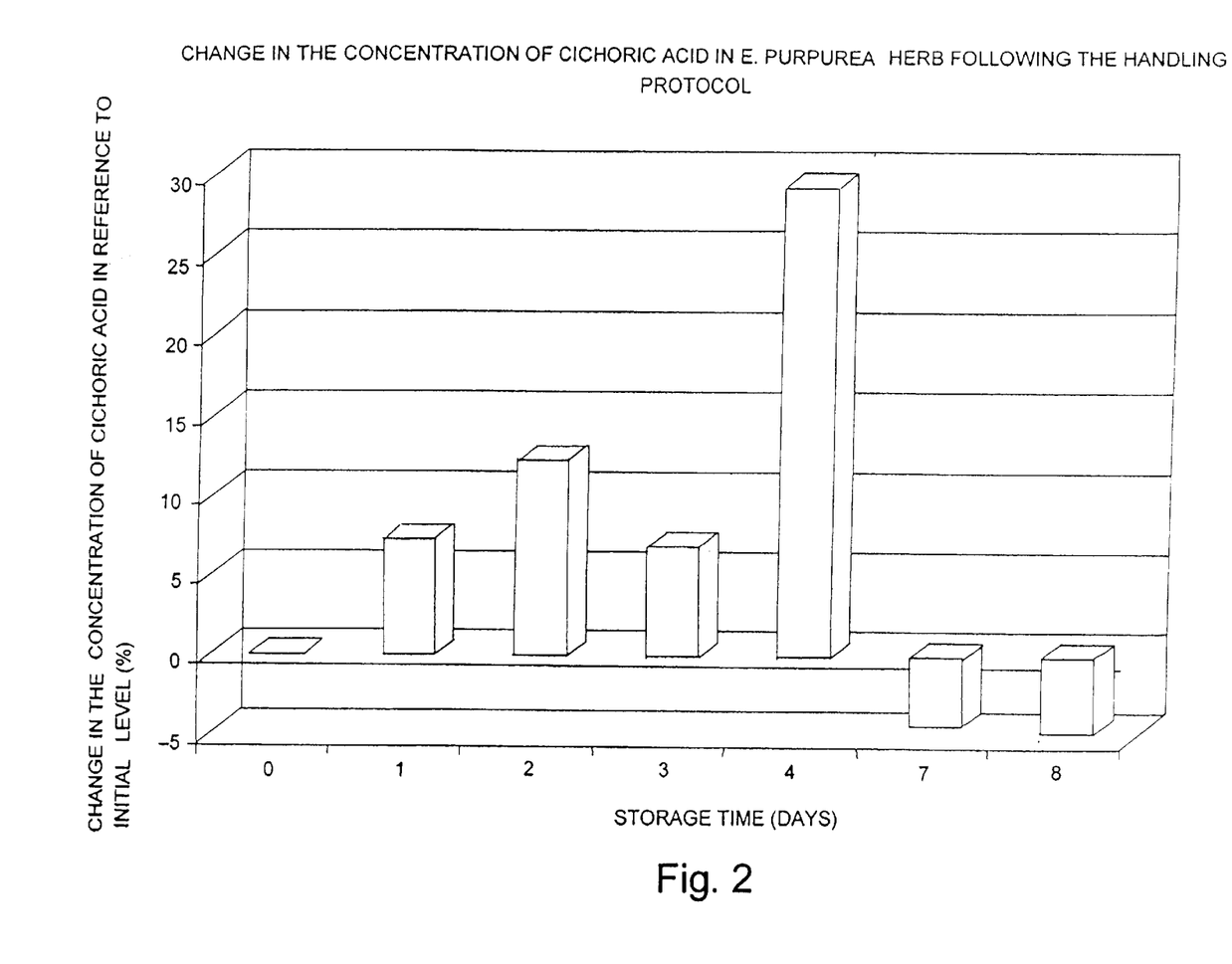
FIG. 2 is a graph showing the percent increase of cichoric acid in an *E. purpurea* herb after undergoing the handling protocol.
Figure 3:
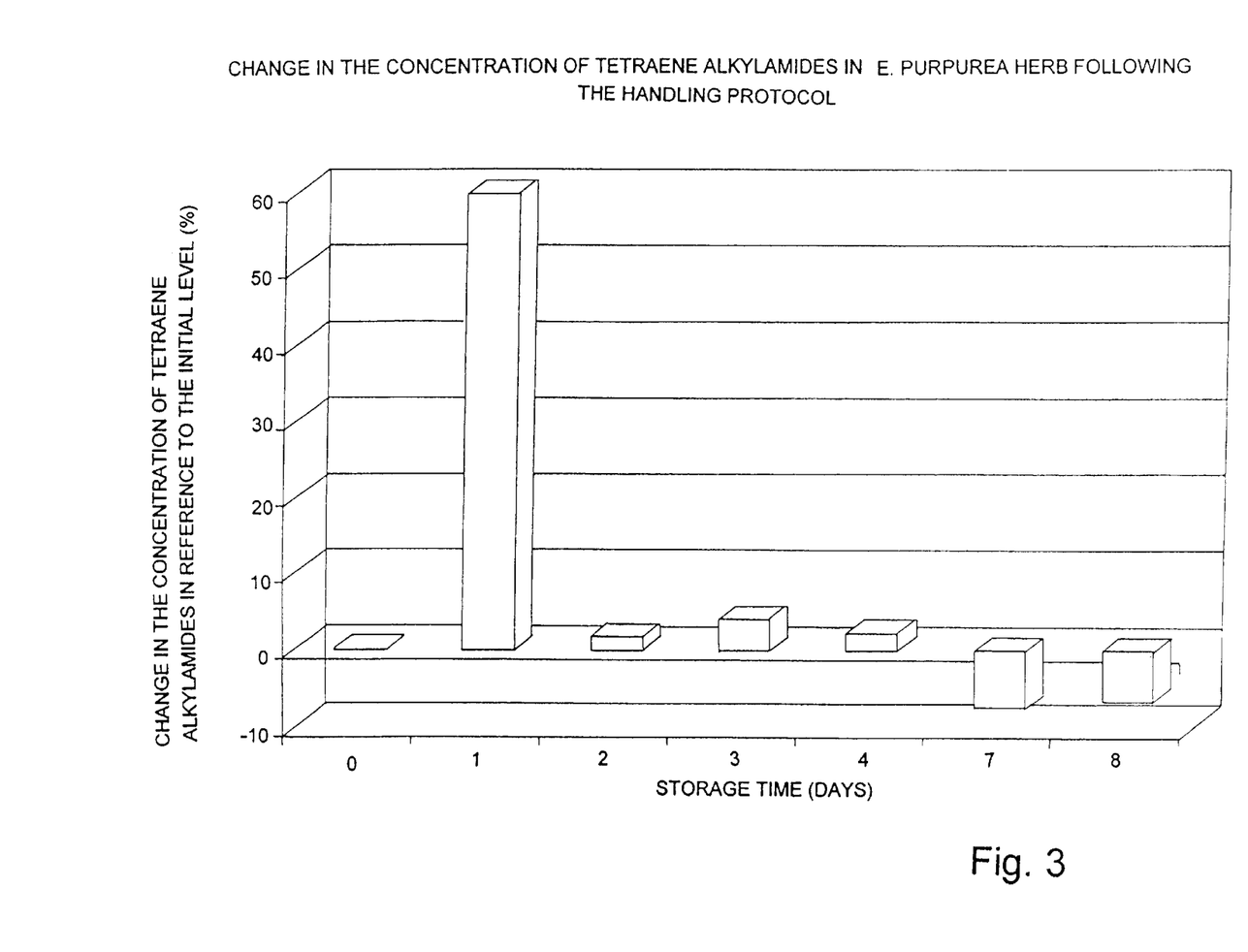
FIG. 3 is a graph showing the percent increase of tetraene alkylamides in an *E. purpurea* herb after undergoing the handling protocol.
Figure 4:
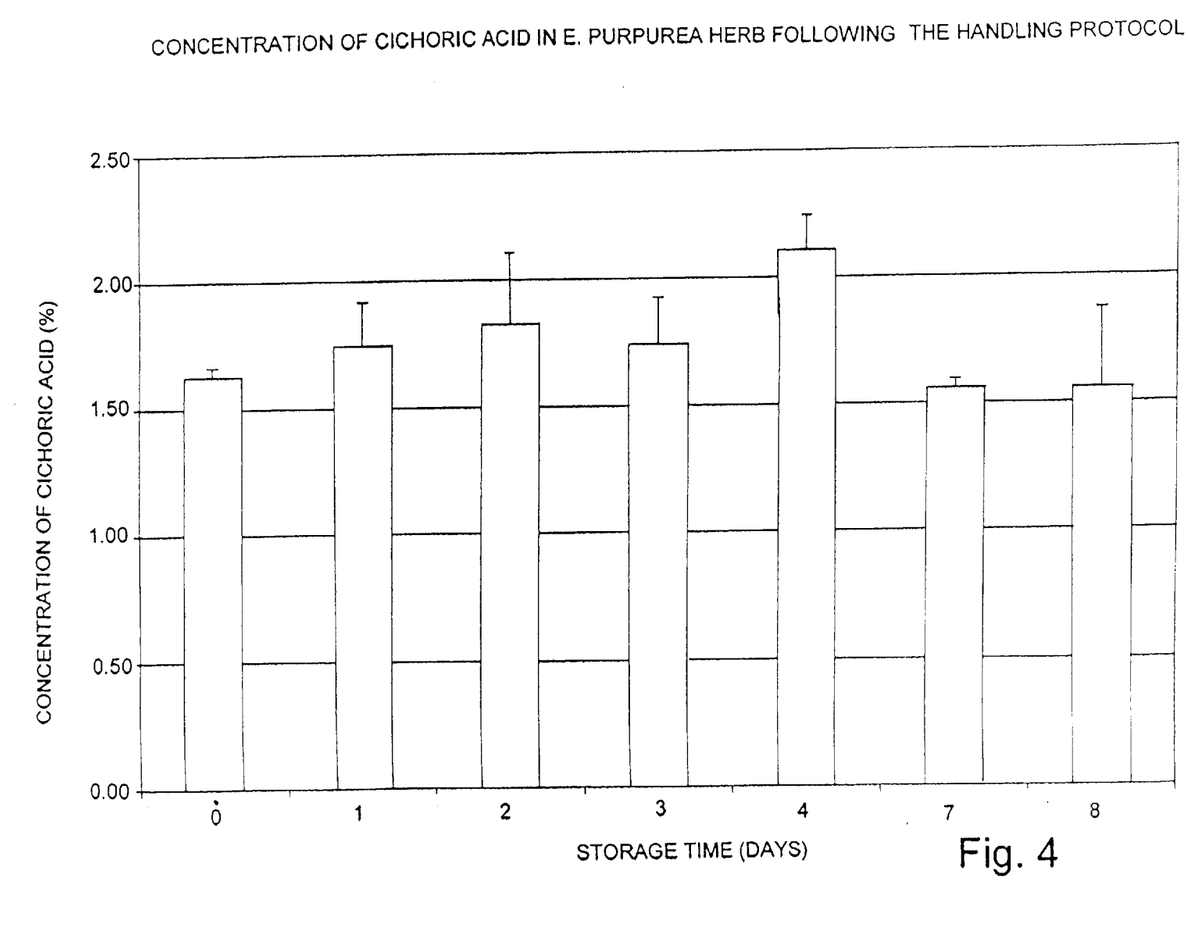
FIG. 4 is a graph showing the concentration of cichoric acid in an *E. purpurea* herb grown in Lakeview, Calif. on days 0 to 8.

*E. purpurea* was grown at the Nutrilite Division of Amway Corporation in Lakeview, Calif. The plant was harvested about 5 inches from the ground with a Befco Flail Mower and chopped into fragments with the same machine. Within 24 hours, about 40 kilograms of the chopped plant fragments were placed in a 40 kilogram polythylene bag having several 2½ inch slits. The polyethylene bag having the plant fragments was stored at 3 degrees Celcius with a controlled relative humidity of 84% for 8 days. As shown in FIG. 2 and FIG. 3, Echinacea plant fragments that underwent one day of the handling protocol showed about a 7% increase in cichoric acid and about a 60% increase of tetraene alkylamides. As shown in FIG. 2, Echinacea plant fragments that underwent fours days of the handling protocol to yield higher cichoric acid concentrations showed about a 30% increase in cichoric acid. The concentrations of cichoric acid and tetraene alkylamides are shown below in Table 1 and FIG. 4; and Table and FIG. 5.

TABLE 1

Concentration of Cichoric Acid in *E. purpurea* after Handling Protocol

| Storage Time (days) | Concentration (%) |
| --- | --- |
| 0 | 1.7 |
| 1 | 1.8 |
| 2 | 1.9 |
| 3 | 1.8 |
| 4 | 2.1 |
| 7 | 1.6 |
| 8 | 1.6 |

TABLE 2

Concentration of Tetraene Alkylamides in *E. purpurea* after Handling Protocol

| Storage Time (days) | Concentration (ppm) |
| --- | --- |
| 0 | 340 |
| 1 | 550 |
| 2 | 340 |
| 3 | 350 |
| 4 | 340 |
| 7 | 310 |
| 8 | 310 |

It is to be understood that the foregoing specification of this invention is illustrative and has been described in relation to certain preferred embodiments. It will be apparent to those skilled in the art that the invention is susceptible to alteration and that certain other details described herein can vary considerably without departing from the basic principles of the invention as defined in the following claims.

What is claimed is:

1. A method of increasing the concentration of cichoric acid, tetraene alkylamides, or a combination thereof in Echinaceas comprising the steps of:
    (a) harvesting an Echinacea plant;
    (b) separating the Echinacea plant into fragments;
    (c) placing the fragments in a container providing semi-aerobic conditions therein; and
    (d) storing the fragments at a temperature range of about 0 degrees Celcius to about 10 degrees Celcius and at a relative humidity level of about 45% to about 85% for about 12 to about 100 hours.

2. The method of claim 1, wherein the plant is selected from the group consisting of *Echinacea purpurea, Echinacea angustifolia, Echinacea pallida*, and mixtures thereof.

3. The method of claim 1, wherein the separating step includes chopping the plant.

4. The method of claim 1, wherein the plant has root portions, wherein the root portions are chopped.

5. The method of claim 1, wherein the harvesting and separating process occur simultaneously.

6. The method of claim 1, wherein the relative humidity level is about 84%.

7. The method of claim 1, wherein the temperature is about 3 degrees Celcius.

8. The method of claim 1, wherein the plant fragments are stored for about 24 hours.

9. The method of claim 1, wherein the plant fragments are stored for about 96 hours.

10. A method of increasing the concentrations of cichoric acid, dodeca-2E, 4E, 8Z, 10E-tetraenoic acid isobutylamide, and dodeca-2E, 4E, 8Z, 10Z-tetraenoic acid isobutylamide in Echinacea postharvest, comprising the steps of:
    (a) harvesting an Echinacea plant;
    (b) chopping the Echinacea plant to obtain plant fragments; and
    (c) storing the Echinacea plant fragments in a container providing semi aerobic conditions at about 3 degrees Celsius with a relative humidity of 84% for about 12 to about 100 hours.

11. An Echinacea plant material prepared according to the process of claim 1 comprising increased concentrations of cichoric acid and tetraene alkylamides per gram of said Echinacea plant material when compared to original postharvest concentrations of cichoric acid and tetraene alkylamides per gram of said Echinacea plant material.

12. The Echinacea plant material of claim 11 wherein the increase comprises:
    (a) at least about a 1% increase in concentration of cichoric acid per gram of the plant material when compared to original postharvest concentration of cichoric acid per gram of the plant material; and
    (b) at least about a 1% increase in concentration of tetraene alkylamides per gram of the plant material when compared to original postharvest concentration of tetraene alkylamides per gram of the plant material.

13. An Echinacea material produced by the process of claim 10.

* * * * *

UNITED STATES PATENT AND TRADEMARK OFFICE
CERTIFICATE OF CORRECTION

Page 1 of 1

PATENT NO. : 6,306,443 B1
DATED : October 23, 2001
INVENTOR(S) : Brovelli et al.

It is certified that error appears in the above-identified patent and that said Letters Patent is hereby corrected as shown below:

Column 9,
Line 30, "Befco Fail Mowe 1" should be -- Befco Fail Mower 1 --

Figure 5:
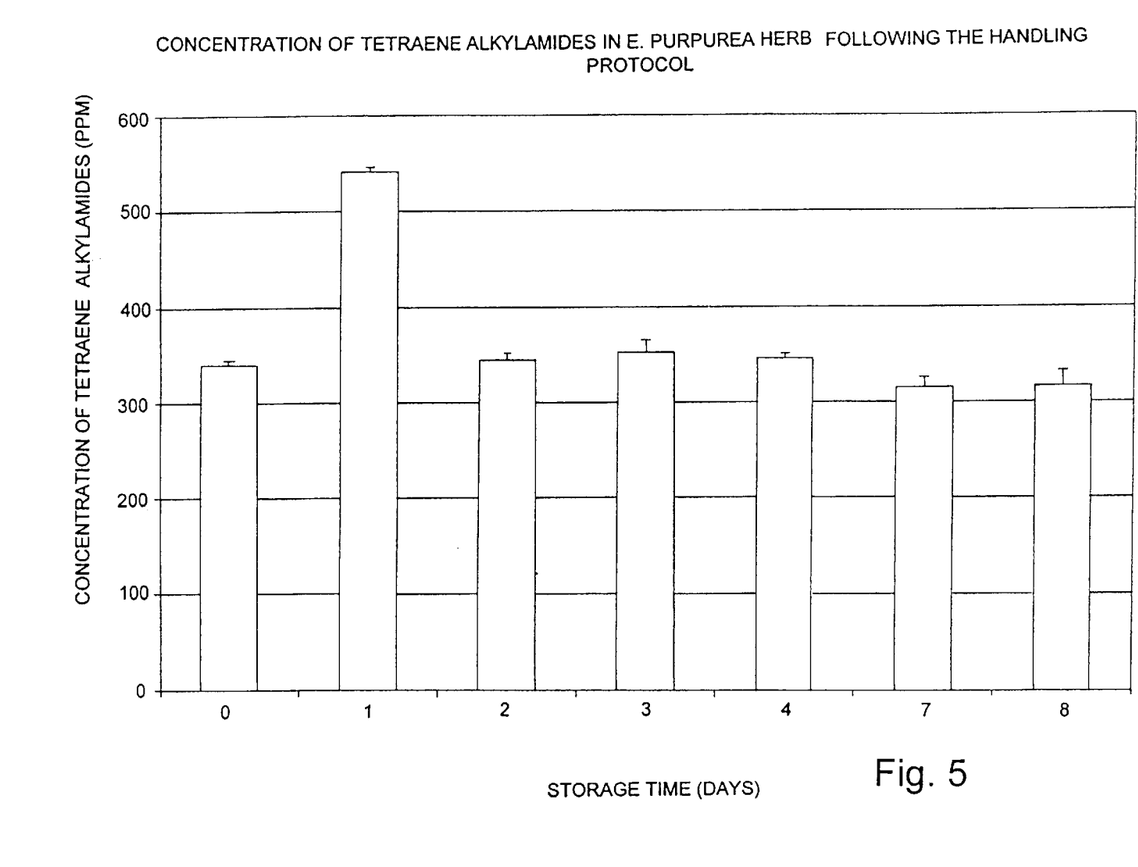
FIG. 5 is a graph showing the concentration of tetraene alkylamides in an *E. purpurea* herb grown in Lakeview, Calif. on days 0 to 8.

Column 11,
Line 3, "Table and FIG. 5." should be -- Table 2 and FIG 5 --
Line 41, "Echinaceas" should be -- Echinacea --

Drawings,
Fig. 1, reference box 3, "Polyethyline" should be -- Polyethylene --

Signed and Sealed this

Twenty-first Day of May, 2002

Attest:

JAMES E. ROGAN
Director of the United States Patent and Trademark Office

Attesting Officer